United States Patent [19]

Granados Jarque et al.

[11] 4,179,565

[45] Dec. 18, 1979

[54] 2,5-DIMETHYL-BENZO[b]-THIENO[2,3-f]MORPHAN AND PRECURSORS THEREOF

[75] Inventors: Ricardo Granados Jarque, Barcelona; Mercedes Alvarez Domingo, San Juan Despi; Juan Bosch Cartes, Barcelona; Cristóbal Martinez Roldán; Fernando Rabadan Peinado, both of Madrid, all of Spain

[73] Assignee: Laboratorios Made, S.A., Madrid, Spain

[21] Appl. No.: 871,653

[22] Filed: Jan. 23, 1978

[30] Foreign Application Priority Data

Feb. 25, 1977 [ES] Spain .................................... 456.283

[51] Int. Cl.² .................... C07D 495/08; C07D 409/06
[52] U.S. Cl. ................................ 546/63; 424/263; 424/267; 546/274; 549/49

[58] Field of Search .................. 260/DIG. 13, 293.54, 260/294.8 C; 424/263, 267; 546/63, 274

[56] References Cited

U.S. PATENT DOCUMENTS 3,382,249  5/1968  Albertson ........................ 260/293.54

OTHER PUBLICATIONS

Montzka, T., et al., *J. Het. Chem.*, 11, 853–855, (1974).
Perry, R., et al., *J. Med. Chem.*, 10, 1184–1186, (1967).

*Primary Examiner*—John M. Ford
*Assistant Examiner*—Richard A. Schwartz
*Attorney, Agent, or Firm*—Ladas, Parry, Von Gehr, Goldsmith & Deschamps

[57] ABSTRACT

2,5-Dimethyl-benzo[b]thieno[2,3-f]morphan and the precursors thereof, 2-(3-benzo[b]thienylmethyl)-1,4-dimethyl-1,2,3,6-tetrahydropyridine and 2-(3-benzo[b]-thienylmethyl)-1,4-dimethyl-1,2,5,6-tetrahydropyridine, useful as analgesic agents, are disclosed.

4 Claims, No Drawings

2,5-DIMETHYL-BENZO[b]-THIENO[2,3-f]MORPHAN AND PRECURSORS THEREOF

The present invention relates to the preparation of 2,5-dimethyl-benzo[b]thieno[2,3-f]morphan (I) to the preparation of two of its intermediates, 2-(3-benzo[b]-thienylmethyl)-1,4-dimethyl-1,2,3,6-tetrahydropyridine (II) and 2-(3-benzo[b]thienylmethyl)-1,4-dimethyl-1,2,5,6-tetrahydropyridine (III) and the addition salts thereof with pharmacologically acceptable acids.

The mentioned compounds are new substances, with interest as analgesics, and are prepared according to the following reaction sequence:

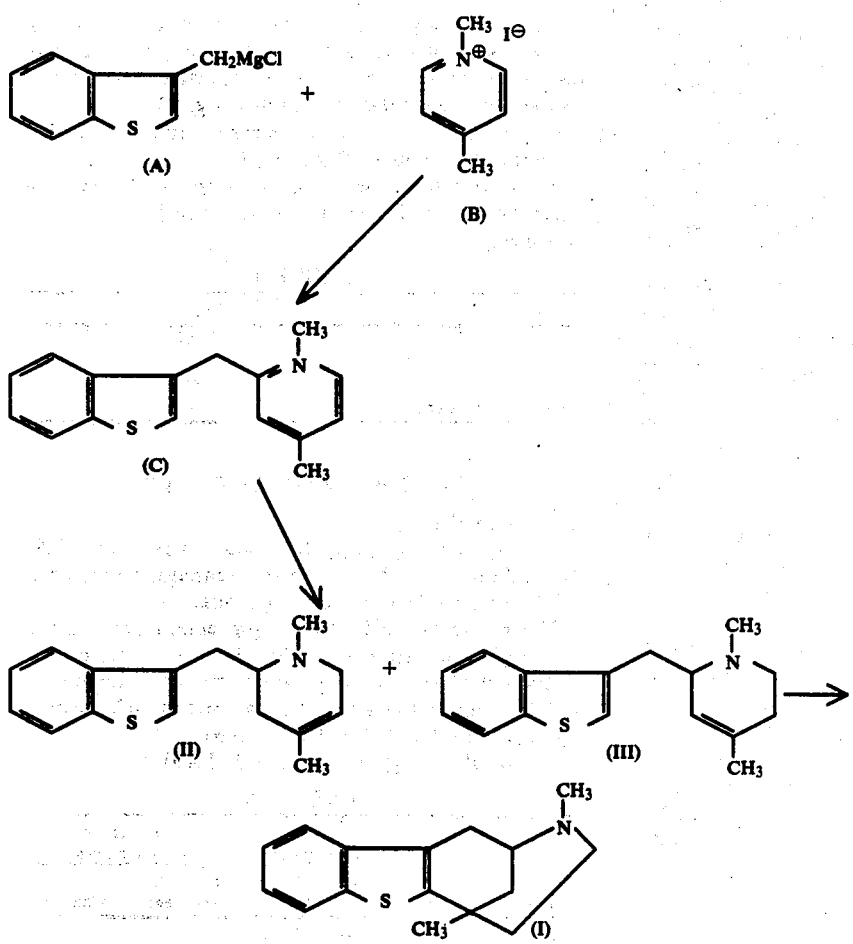

In the first part of the process 3-chloromethyl-benzo[b]-thiophene magnesiane (A) is obtained under conditions of high dilution and in an inert atmosphere and is reacted at reflux temperature with 1,4-dimethyl-pyridinium iodide (B) in anhydrous ether, obtaining the unstable intermediate 2-(3-benzo-[b]thienylmethyl)-1,4-dimethyl-1,2-dihydropyridine (C). Said intermediate, without subsequent purification, is reduced in a basic medium with sodium borohydride in an aqueous methanol solution. The organic layer gives a mixture from which 2-(3-benzo[b]-thienylmethyl)-1,4-dimethyl-1,2,3,6-tetrahydropyridine (II) and 2-(3-benzo[b]-thienylmethyl)-1,4-dimethyl-1,2,5,6-tetrahydropyridine (III) are separated by distillation and subsequent fractional crystallisation of the corresponding picrates.

In a following stage of the process, the previously obtained raw mixture is heated to 135° C. for 12 h. in the presence of a strong acid, for example 48% aqueous hydrobromic acid. It is poured over ice and water, rendered alkaline with ammonium hydroxide and extracted with ether, yielding 2,5-dimethyl-benzo[b]-thieno[2,3-f]-morphan (I).

The following examples are given by way of illustration only and in no way are they to be considered as limiting the scope of the invention.

EXAMPLE 1

Preparation of 2-(3-benzo[b]thienylmethyl)-1,4-dimethyl-1,2,3,6-tetrahydropyridine (II) and of 2-(3-benzo[b]thienylmethyl)-1,4-dimethyl-1,2,5,6-tetrahydropyridine (III)

The "modified cyclic reactor", which comprises a continuous flow column provided with a dropping funnel, coolant and a reaction flask, was used to obtain 3-benzo[b]thienylmethyl-magnesium chloride. The column of the reactor is packed with 70 gr. of magnesium in chips, alternating with thin layers of mercuric chloride, and is covered with a saturated solution of mercuric chloride in anhydrous ether. It is left standing for 48 h., 250 ml. of anhydrous ether then being placed in the flask and refluxed for 2 h. The flask is replaced by another provided with mechanical stirring, in which 19 gr. of 1,4-dimethylpyridinium iodide in suspension with 300 ml. of anhydrous ether are placed. 14 gr. of 3-chloromethylbenzo[b]thiophene dissolved in 250 ml. of anhydrous ether are placed in a dropping funnel. Some ml. of halide solution are added on the magnesium column and when it is observed that the reaction begins the flask is heated to the reflux temperature, continuing the addition slowly for 5 h. The nitrogen atmosphere is maintained in the system throughout the process.

After completing the addition, reflux is continued for 4 h.; the resulting ethereal solution is poured over 250 ml. of aqueous solution of ammonium chloride and ice; the mixture is rendered alkaline with concentrated ammonium hydroxide and is extracted with ether. The ethereal solution is extracted with 10% hydrochloric acid; the aqueous layer is rendered alkaline with ammonium hydroxide and is extracted with ether. The ethereal extract, dried with magnesium sulphate and evaporated, gives 11.3 gr. of the unstable intermediate 2-(3-benzo-[b]thienylmethyl)-1,4-dimethyl-1,2-dihydropyridine. 30 ml. of 1 N sodium hydroxide and 2 gr. of sodium borohydride are added to a solution of 11.3 gr. of said intermediate in 50 ml. of methanol. The mixture is heated to reflux temperature and stirred for 12 h. The resulting product is extracted with ether and dried with magnesium sulphate. Once the ether is evaporated, 7.5 gr. of a mixture of tetrahydropyridines are obtained. Overall yield of the process: 38.0%. Said mixture is distilled (4.5 gr) (125°–180° C./0.1 mm/Hg) and the picrate is then precipitated. Following successive recrystallisations from ethanol, 2-(3-benzo[b]thienylmethyl)-1,4-dimethyl-1,2,3,6-tetrahydropyridine picrate (II) is separated. An analytical sample recrystallised from absolute ethanol has a melting point of 162°–164° C.

Analysis calculated for $C_{22}H_{22}O_7N_4S$. Calculated: C=54.34%; H=4.52%; N=11.50%; S=6.59%. Found: C=54.21%; H=4.84%; N=11.39%; S=6.33%.

The mother liquors of the first recrystallisations yield a solid which, following several recrystallisations from ethanol-ethyl acetate, gives 2-(3-benzo[b]thienylmethyl)-1,4-dimethyl-1,2,5,6-tetrahydropyridine picrate (III), which has a melting point of 158°–161° C.

Analysis calculated for $C_{22}H_{22}O_7N_4S$ (III). Calculated: C=54.34%; H=4.52%; N=11.50%; S=6.59%. Found: C=54.32%; H=4.73%; N=11.50%; S=6.34%.

EXAMPLE 2

Preparation of 2,5-dimethyl-benzo[b]thieno-[2,3-f]morphan (I)

A solution of 3 gr. of the previously obtained mixture of tetrahydropyridines in 42 ml. of 48% aqueous hydrobromic acid is heated to 130°–5° C. for 12 h. The mixture is left to cool, is poured over water and ice, is rendered alkaline with ammonium hydroxide and is extracted with ether. The ethereal solution is dried with magnesium sulphate and the solvent is evaporated, giving 3 gr. of an oil which is purified by distillation (1.1 gr) (99°–160° C./0.07 mm/Hg). Yield: 36.6%. The hydrochloride is precipitated and purified by recrystallisation from acetone-ether, giving a solid with a melting point of 225°–230° C.

Analysis calculated for $C_{16}H_{20}NSCl \cdot \frac{1}{2}H_2O$. Calculated: C=63.48%; H=6.95; N=4.62%. Found: C=63.48%; H=7.23%; N=4.48%.

PHARMACOLOGY OF THE PRODUCTS OF THE INVENTION

PRODUCTS

I—2,5-dimethyl-benzo[b]thieno[2,3-f]morphan.
II—2-(3-benzo[b]thienylmethyl)-1,4-dimethyl-1,2,3,6-tetrahydropyridine.
III—2-(3-benzo[b]thienylmethyl)-1,4-dimethyl-1,2,5,6-tetrahydropyridine.

They are products with analgesic activity. The activity of these products has been studied by comparing them with that of dextropropoxyphene.

A—ACUTE TOXICITY

Acute toxicity studies were performed on I.C.R. Swiss albino mice of both sexes weighing 30±2 g, kept fasting for 24 hours prior to the experiment. The room temperature and relative humidity were kept constant. The products were administered intraperitoneally, counting the number of deaths 48 hours after the treatment. The calculation of lethal dose 50 ($LD_{50}$) was made by the Litchfield-Wilcoxon test. The results obtained were:

TABLE 1

| Product | $LD_{50}$ (mg/kg) |
|---|---|
| I | 35.2 |
| II | 916.3 |
| III | 275 |
| Dextropropoxyphene | 140 |

B—ANALGESIC ACTIVITY

1. Thermal analgesia

The thermal analgesic effect was studied on I.C.R. Swiss albino mice. The hot plate technique was used at 55° C. Batches of 10 mice were made.

The products under study were administered intraperitoneally and after 30 minutes the mice were placed on the hot plate, counting the number of seconds they took to jump. Batches of control animals which are only injected with distilled water are used.

The results are given in tables 2, 3 and 4.

TABLE II

| | | Jumping time in sec. (1) | Significance of differences | |
|---|---|---|---|---|
| Treatment | Dose | $\bar{x} \pm$ S.E.M. | Dextropropoxyphene | Control |
| Control | — | 64 ± 7.919 | — | — |
| Dextropropoxyphene | 50mg/kg | 164 ± 7.319 | — | p<0.00005 |
| Product I | 50mg/kg | 168.67 ± 11.334 | N.S. | p<0.00005 |

(1) Mean values ± standard error of the mean.

Product I has analgesic activity which is not significantly different from that of dextropropoxyphene.

TABLE III

| | | Jumping time in seconds | Significance of differences | |
|---|---|---|---|---|
| Treatment | Dose | $\bar{x} \pm$ S.E.M. | Dextropropoxyphene | Control |
| Control | — | 48.8 ± 5.033 | — | — |
| Dextropropoxyphene | 50mg/kg | 91.3 ± 7.894 | — | p<0.0005 |
| Product II | 50mg/kg | 63 ± 8.368 | p<0.05 | N.S. |

Product II is lacking thermal analgesic activity.

TABLE IV

| Treatment | Dose | Jumping time in sec. $\bar{x} \pm$ S.E.M. | Significance of differences | |
| --- | --- | --- | --- | --- |
| | | | Dextropropoxyphene | Control |
| Control | — | 48.8± 5.033 | — | — |
| Dextropropoxyphene | 50mg/kg | 91.3 ± 7.894 | — | p<0.0005 |
| Product III | 50mg/kg | 48.9 ± 5.292 | p<0.0005 | |

Product III is lacking thermal analgesic activity.

2. Chemical analgesia

The analgesic effect was studied on I.C.R. Swiss albino mice with the acetic acid writhing technique. Batches of 10 mice were made.

The products under study were administered intraperitoneally and after 30 minutes 0.25 ml of 1% acetic acid are injected intraperitoneally. A batch of control animals which only receive acetic acid is used. The number of writhes in each mouse is counted 20 minutes after administration of the acetic acid.

The results are given in tables 5, 6 and 7.

TABLE V

| Treatment | Dose | No. of writhes $\bar{x} \pm$ S.E.M. | Significance of differences | |
| --- | --- | --- | --- | --- |
| | | | Control | Dextropropoxyphene |
| Control | — | 101.4 ± 8.973 | — | — |
| Dextropropoxyphene | 25mg/kg | 21.5 ± 5.929 | p<0.00005 | — |
| Product I | 25mg/kg | 3.1 ± 1.234 | p<0.00005 | p<0.01 |

Product I has greater analgesic activity then dextropropoxyphene.

TABLE VI

| Treatment | Dose | No. of writhes $\bar{x} \pm$ S.E.M. | Significance of differences | |
| --- | --- | --- | --- | --- |
| | | | Control | Dextropropoxyphene |
| Control | — | 109.9 ± 6.362 | — | — |
| Dextropropoxyphene | 25mg/kg | 27.8 ± 8.365 | p<0.00005 | — |
| Product II | 25mg/kg | 41.2 ± 6.024 | p<0.00005 | N.S. |

The analgesic activity of product II is not significantly different from that of dextropropoxyphene.

TABLE VII

| Treatment | Dose | No. of writhes $\bar{x} \pm$ S.E.M. | Significance of differences | |
| --- | --- | --- | --- | --- |
| | | | Control | Dextropropoxyphene |
| Control | — | 109.9 ± 6.362 | — | — |
| Dextropropoxyphene | 25mg/kg | 27.8 ± 8.365 | p<0.00005 | — |
| Product III | 25mg/kg | 22.5 ± 6.263 | p<0.00005 | N.S. |

The analgesic activity of product III is not significantly different from that of dextropropoxyphene.

We claim:

1. A compound selected from the group consisting of 2,5-dimethyl-benzo[b]-thieno[2,3-f]morphan (I), 2-(3-benzo[b]thienylmethyl)-1,4-dimethyl-1,2,3,6-tetrahydropyridine (II) or 2-(3-benzo[b]-thienylmethyl)-1,4-dimethyl-1,2,5,6-tetrahydropyridine (III) or a pharmacologically acceptable acid addition salt thereof.

2. The compound defined in claim 1 which is 2,5-dimethyl-benzo[b]-thieno[2,3-f]morphan or a pharmacologically acceptable acid addition salt thereof.

3. The compound defined in claim 1 which is 2-(3-benzo[b]thienylmethyl)-1,4-dimethyl-1,2,3,6,-tetrahydropyridine or a pharmacologically acceptable acid addition salt thereof.

4. The compound defined in claim 1 which is 2-(3-benzo[b]thienyl-methyl-1,4-dimethyl-1,2,5,6-tetrahydropyridine or a pharmacologically acceptable acid addition salt thereof.

* * * * *